(12) United States Patent
Sniffin et al.

(10) Patent No.: US 10,307,038 B2
(45) Date of Patent: Jun. 4, 2019

(54) SYSTEM AND METHOD FOR PERFORMING SURGICAL PROCEDURES WITH A MODULAR SURGICAL SYSTEM

(75) Inventors: Kevin Sniffin, Danbury, CT (US); Eric Taylor, East Hampton, CT (US); Peter Hathaway, Lebanon, CT (US); Emily Davis, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 986 days.

(21) Appl. No.: 13/412,061

(22) Filed: Mar. 5, 2012

(65) Prior Publication Data

US 2012/0253116 A1 Oct. 4, 2012

Related U.S. Application Data

(60) Provisional application No. 61/468,868, filed on Mar. 29, 2011.

(51) Int. Cl.
*A61B 1/008* (2006.01)
*A61B 1/00* (2006.01)
(Continued)

(52) U.S. Cl.
CPC .......... *A61B 1/00066* (2013.01); *A61B 1/008* (2013.01); *A61B 1/0052* (2013.01);
(Continued)

(58) Field of Classification Search
CPC .............. A61B 18/14; A61B 17/00234; A61B 17/3421; A61B 18/1445; A61B 2019/2211; A61B 2017/003; A61B 2019/2276; A61B 2017/00464; A61B 2017/00734; A61B 2018/00184; A61B 2018/1495; A61B 2018/1226; A61B 2019/4815; A61B 2018/0094; A61B 1/0052; A61B 1/00105; A61B 1/00066; A61B 2017/00367; A61B 17/2909; A61B 2018/0091; A61B 1/005; A61B 2017/0046; A61B 1/00; A61B 1/00098; A61B 1/0051–0053;
(Continued)

(56) References Cited

U.S. PATENT DOCUMENTS 4,091,880 A * 5/1978 Troutner et al. .............. 173/217
4,911,148 A * 3/1990 Sosnowski ........... A61B 1/0051
600/136

(Continued)

FOREIGN PATENT DOCUMENTS

EP 2 044 890 A1 4/2009

*Primary Examiner* — Sarah W Aleman
*Assistant Examiner* — Rachel S Highland

(57) ABSTRACT

A surgical system is provided including a reusable handle assembly having a controller and a reusable cannula assembly configured to be operatively connected to and steerable by the reusable handle assembly. Additionally, the surgical system includes a plurality of surgical instruments configured to be inserted through the reusable handle assembly and configured to advance a length of the reusable cannula assembly, such that the plurality of surgical instruments are engaged with at least one trigger mechanism of the reusable handle assembly. The handle assembly, the cannula assembly, and the plurality of surgical instruments are modular components configured to be releasably or removably coupled or interconnected to each other.

21 Claims, 3 Drawing Sheets

(51) Int. Cl.
  *A61B 1/005* (2006.01)
  *A61B 17/00* (2006.01)
  *A61B 17/34* (2006.01)
  *A61B 18/00* (2006.01)
  *A61B 18/12* (2006.01)
  *A61B 18/14* (2006.01)
  *A61B 34/00* (2016.01)
  *A61B 34/30* (2016.01)
  *A61B 90/00* (2016.01)

(52) U.S. Cl.
  CPC ...... *A61B 1/00098* (2013.01); *A61B 1/00105* (2013.01); *A61B 17/00234* (2013.01); *A61B 17/3421* (2013.01); *A61B 18/14* (2013.01); *A61B 18/1445* (2013.01); *A61B 2017/003* (2013.01); *A61B 2017/00464* (2013.01); *A61B 2017/00734* (2013.01); *A61B 2018/0094* (2013.01); *A61B 2018/00184* (2013.01); *A61B 2018/1226* (2013.01); *A61B 2018/1495* (2013.01); *A61B 2034/301* (2016.02); *A61B 2034/742* (2016.02); *A61B 2090/0803* (2016.02)

(58) Field of Classification Search
  CPC ..... A61B 1/0058; A61B 1/008; A61B 1/0018; A61B 1/01
  USPC .............................................. 606/1, 130, 205
  See application file for complete search history.

(56) References Cited

U.S. PATENT DOCUMENTS

| | | | |
|---|---|---|---|
| 5,195,541 A * | 3/1993 | Obenchain | 128/898 |
| 5,527,279 A * | 6/1996 | Imran | A61M 25/0158 604/95.01 |
| 5,658,249 A | 8/1997 | Beland et al. | |
| 5,752,972 A | 5/1998 | Hoogeboom | |
| 5,827,319 A | 10/1998 | Carlson et al. | |
| 5,882,333 A * | 3/1999 | Schaer | A61M 25/0144 600/434 |
| 5,931,849 A | 8/1999 | Desvignes et al. | |
| 5,954,259 A | 9/1999 | Viola et al. | |
| 6,090,107 A | 7/2000 | Borgmeier et al. | |
| 6,248,092 B1 | 6/2001 | Miraki et al. | |
| 7,044,937 B1 | 5/2006 | Kirwan et al. | |
| 7,193,519 B2 | 3/2007 | Root et al. | |
| 7,249,602 B1 * | 7/2007 | Emanuel | 128/898 |
| 7,468,041 B2 | 12/2008 | Rhodes et al. | |
| 7,611,474 B2 * | 11/2009 | Hibner et al. | 600/566 |
| 7,615,067 B2 * | 11/2009 | Lee | A61B 17/062 604/528 |
| 7,757,925 B2 | 7/2010 | Viola et al. | |
| 7,806,835 B2 * | 10/2010 | Hibner et al. | 600/567 |
| 7,922,063 B2 | 4/2011 | Zemlok et al. | |
| D649,635 S | 11/2011 | Cronin et al. | |
| 2001/0031983 A1 | 10/2001 | Brock et al. | |
| 2002/0165549 A1 | 11/2002 | Owusu-Akyaw et al. | |
| 2004/0199051 A1 * | 10/2004 | Weisel | A61B 17/29 600/141 |
| 2006/0278681 A1 | 12/2006 | Viola et al. | |
| 2007/0005002 A1 | 1/2007 | Millman et al. | |
| 2007/0032704 A1 * | 2/2007 | Gandini | A61B 17/0218 600/219 |
| 2007/0135733 A1 * | 6/2007 | Soukup | A61M 25/0136 600/585 |
| 2007/0156019 A1 * | 7/2007 | Larkin | A61B 19/2203 600/104 |
| 2008/0058595 A1 * | 3/2008 | Snoke et al. | 600/114 |
| 2008/0177134 A1 * | 7/2008 | Miyamoto | A61B 17/062 600/104 |
| 2009/0048612 A1 | 2/2009 | Farritor et al. | |
| 2009/0108048 A1 * | 4/2009 | Zemlok et al. | 227/175.1 |
| 2009/0138006 A1 | 5/2009 | Bales et al. | |
| 2009/0157076 A1 * | 6/2009 | Athas | A61B 17/3421 606/41 |
| 2009/0270897 A1 * | 10/2009 | Adams et al. | 606/170 |
| 2010/0069936 A1 | 3/2010 | Palmer et al. | |
| 2010/0262161 A1 * | 10/2010 | Danitz | A61B 1/0053 606/130 |
| 2011/0071349 A1 * | 3/2011 | Drontle et al. | 600/106 |
| 2011/0118544 A1 * | 5/2011 | Adams et al. | 600/104 |
| 2011/0130787 A1 | 6/2011 | Cinquin et al. | |
| 2011/0251606 A1 | 10/2011 | Kerr | |
| 2011/0251632 A1 | 10/2011 | Deville et al. | |
| 2011/0257650 A1 | 10/2011 | Deville et al. | |

* cited by examiner

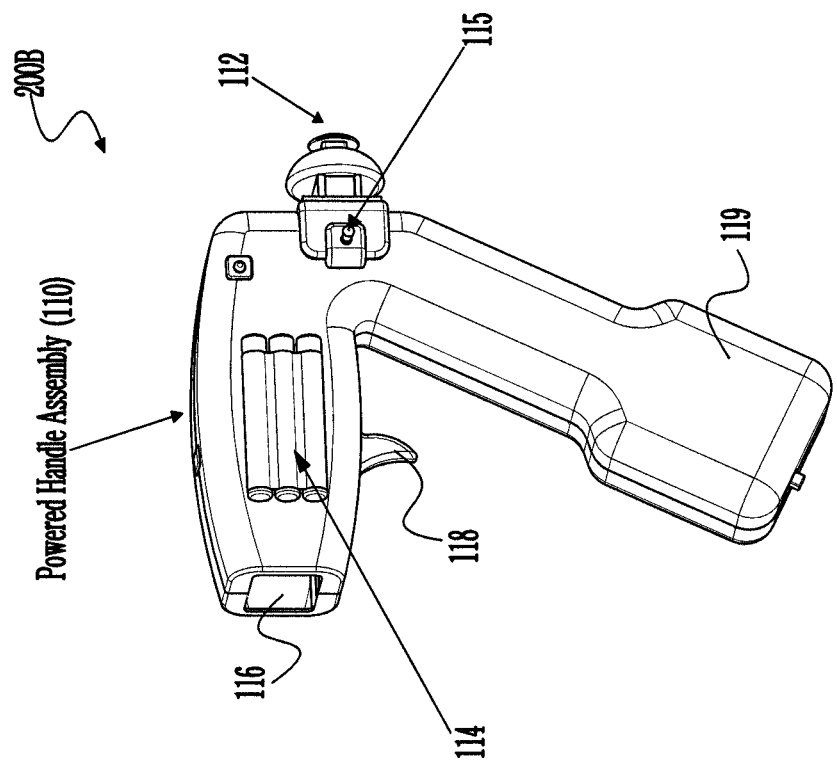
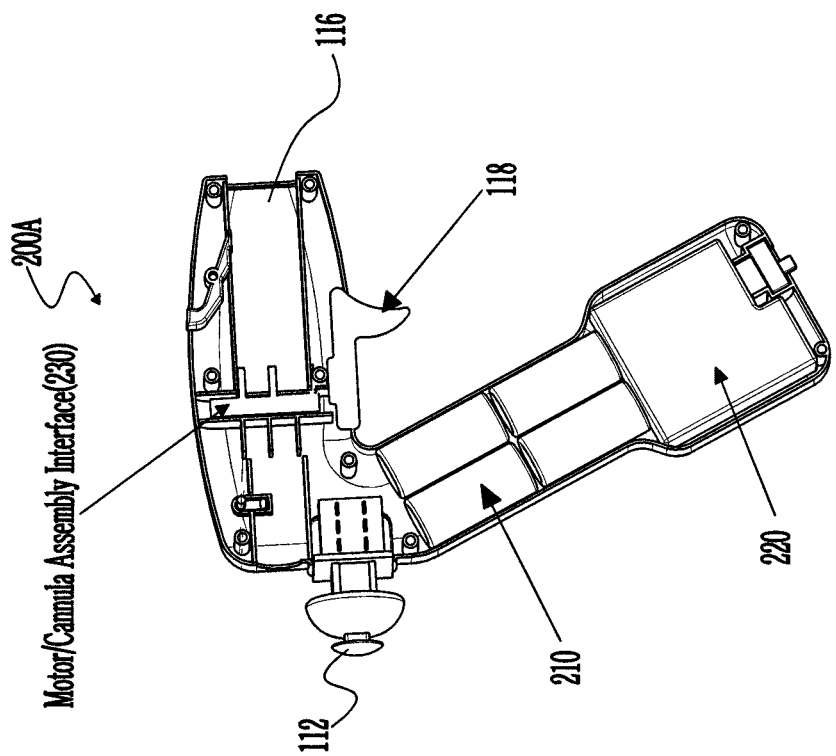

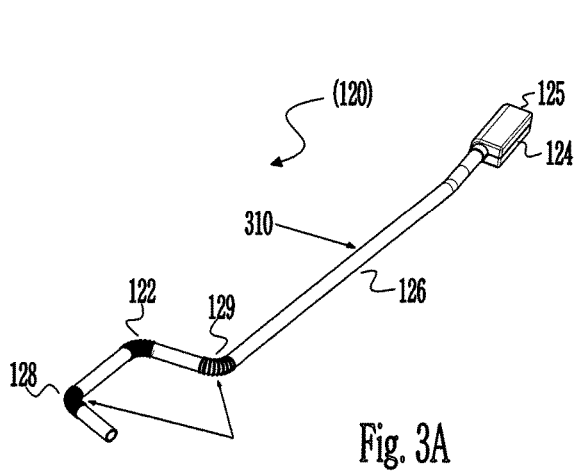
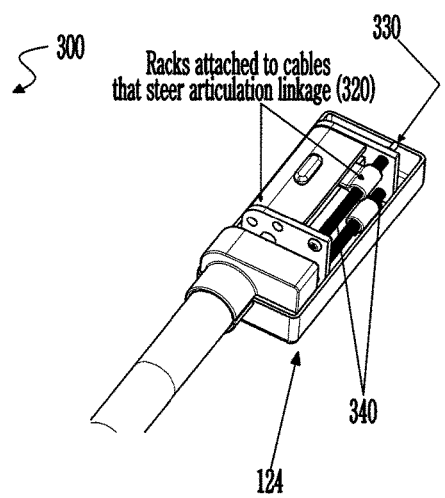
Fig. 3A
Fig. 3B
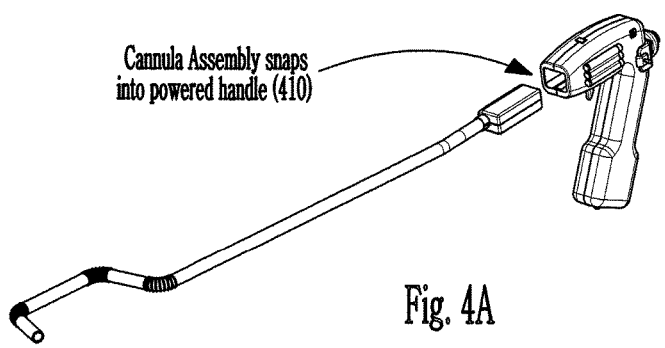
Fig. 4A
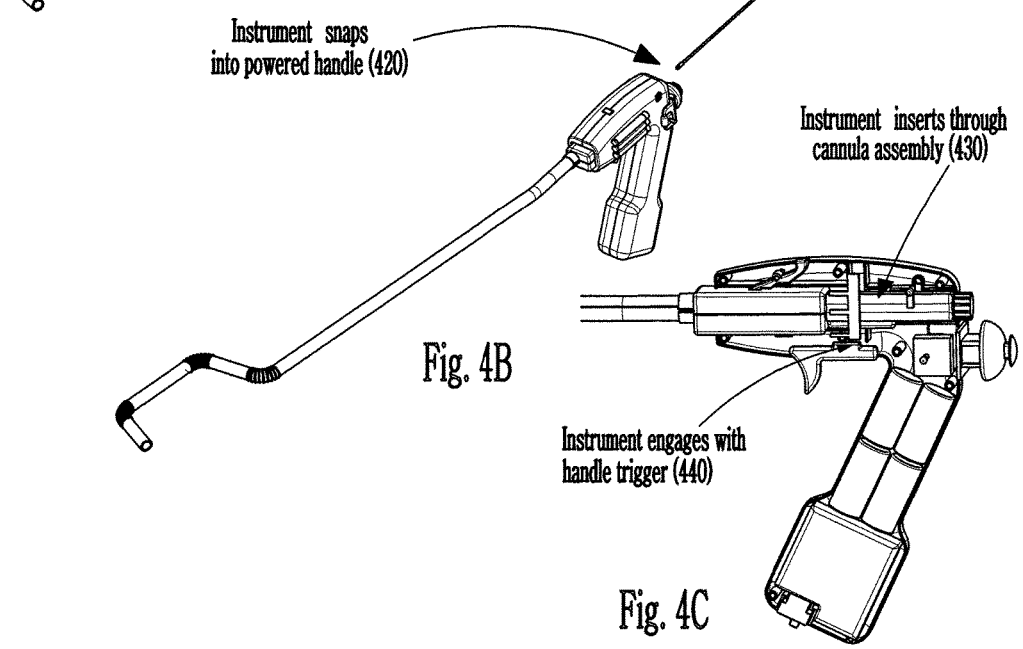
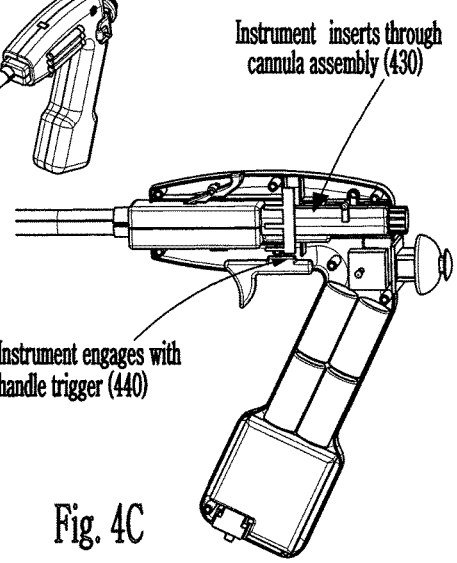
Fig. 4B
Fig. 4C

SYSTEM AND METHOD FOR PERFORMING SURGICAL PROCEDURES WITH A MODULAR SURGICAL SYSTEM

CROSS REFERENCE TO RELATED APPLICATION

The present application claims the benefit of and priority to U.S. Provisional Application Ser. No. 61/468,868, filed on Mar. 29, 2011, the entire contents of which are incorporated herein by reference.

BACKGROUND

Technical Field

The present disclosure relates generally to the field of reposable or reusable surgical instruments. In particular, the disclosure relates to instruments having separable and replaceable components to provide clean, sterile or refurbished surfaces in each instance of use.

Background of Related Art

Surgical instruments are commonly used in open and endoscopic surgical procedures to coagulate, cauterize and seal tissue. Such surgical instruments may typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws.

In use, various tissue-contacting components of surgical instruments tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Surgical instruments that are reposable, or reusable for multiple procedures, reduce the instrumentation costs per procedure. Providing a reusable surgical instrument, however, presents various challenges. For example, the complexity of a surgical instrument tends to result in fairly labor intensive cleaning procedures to prepare the surgical instrument for subsequent use. Improper cleaning may result in dangerous contamination being introduced into the surgical site. Also, some reusable surgical instruments have removable and replaceable components to provide clean surfaces for each use. Many of these surgical instruments require arduous disassembly and reassembly procedures that require extensive training, and may discourage use of the instrument.

SUMMARY

Accordingly, an improved surgical system is provided. The surgical system includes a reusable handle assembly having a controller; a reusable cannula assembly configured to be operatively connected to and steerable by the reusable handle assembly; and a plurality of surgical instruments configured to be inserted through the reusable handle assembly and configured to advance a length of the reusable cannula assembly, such that the plurality of surgical instruments are engaged with at least one trigger mechanism of the reusable handle assembly; wherein the handle assembly, the cannula assembly, and the plurality of surgical instruments are modular components configured to be releasably connected or coupled to each other.

In another exemplary embodiment, an improved surgical system is provided. The surgical system includes a modular handle assembly including a joystick controller, a self-contained battery pack, electronic circuitry, and a motor; a modular cannula assembly configured to be releasably secured to and steerable by the modular handle assembly; and a plurality of surgical instruments configured to be inserted through the modular handle assembly and configured to advance a length of the modular cannula assembly, such that the plurality of surgical instruments are releasably secured to the modular handle assembly; wherein releasable securement is caused by a plurality of mechanical mating mechanisms disposed at proximal and/or distal ends of the modular handle assembly, the modular cannula assembly and the plurality of surgical instruments to enable releasable coupling of the assemblies and instruments.

In another exemplary embodiment a method of performing a surgical procedure is provided. The method includes the steps of releasably securing a modular handle assembly to a modular cannula assembly, the modular handle assembly including a joystick controller, a self-contained battery pack, electronic circuitry, and a motor; inserting at least one surgical instrument through the modular handle assembly; advancing the at least one surgical instrument a length of the modular cannula assembly; releasably securing the at least one surgical instrument to the modular handle assembly; and steering the modular cannula assembly via the joystick controller of the modular handle assembly so as to actuate the at least one surgical instrument.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 2A is a cut-away view of the handle assembly, in accordance with the present disclosure;

FIG. 2B is a side view of the handle assembly, in accordance with the present disclosure;

FIG. 3A is a perspective view of the reusable cannula assembly, in accordance with the present disclosure;

FIG. 3B is a magnified interior view of a proximal end of the reusable cannula assembly of FIG. 3A, in accordance with the present disclosure; and FIGS. 4A-4C are perspective views of the surgical system of FIG. 1, illustrating how the handle assembly, cannula assembly, and surgical instrument are releasably or removably coupled/connected/attached to each other, in accordance with the present disclosure.

DETAILED DESCRIPTION

Figure 1:
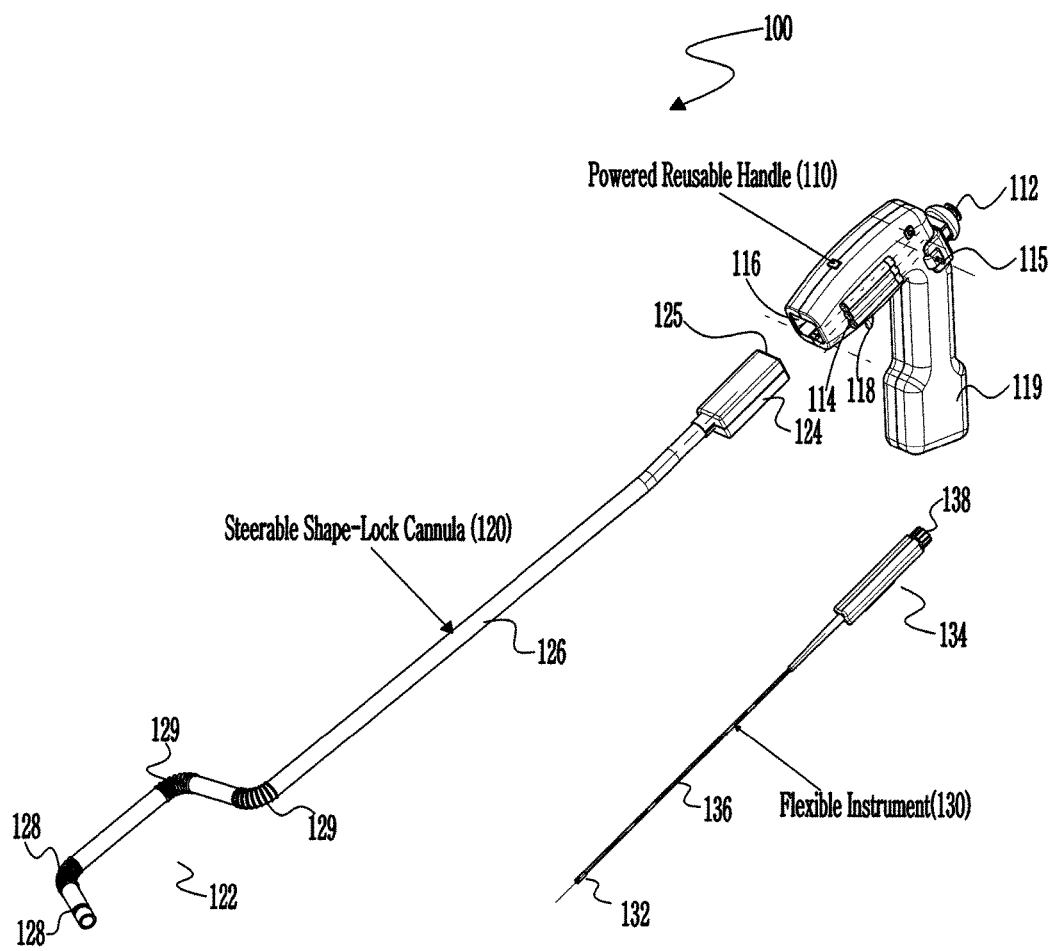
FIG. 1 is a perspective view of a surgical system having a reusable/modular handle assembly, a reusable/modular cannula assembly, and a surgical instrument, in accordance with the present disclosure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

In the exemplary embodiments of the present disclosure, the surgical system includes: 1) a powered reusable handle assembly with a joystick controller and a self-contained battery pack, 2) a reusable and steerable shape locking cannula assembly, and 3) at least one flexible instrument with the ability to swap out and be used within the same reusable handle assembly. The components or units or assemblies are modular and snap together for use and snap apart for cleaning. The cannula assembly is designed to be inserted straight through a single incision and is electronically activated to have a preset "offset" bend, which modifies the angle of approach to be lateral within the abdomen of a patient. Flexible surgical instruments are then guided down and follow the inside shape of the cannula assembly. Distal articulating linkages are then steered by using a controller, such as a joystick controller, to gain precise movement in and around the target surgical site.

In the exemplary embodiments of the present disclosure, through a single incision, the ability to provide lateral traction inside the abdomen without instrument crossover/clashing is achieved. Hand separation and comfort to the end user through powered controls as opposed to manual wrist operation is also achieved. The modular design of the components/assemblies results in cost efficiency by reusing a single motor repeatedly.

Referring to FIG. 1, a surgical system 100 for use in a surgical procedure, e.g., a minimally invasive procedure is illustrated. Surgical system 100 includes a powered reusable handle assembly 110, a steerable reusable cannula assembly 120, and at least one surgical instrument 130.

The powered reusable handle assembly 110 includes a controller 112, a motor 114, a mating mechanism 116, a trigger mechanism 118, and a handle portion 119. The powered reusable handle assembly 110 also includes a switch 115 for activating an initial offset bend of the reusable cannula assembly 120.

The controller 112 of the powered reusable handle assembly 110 may be a joystick mechanism configured to steer a plurality of articulation linkages 128, which are distally disposed on the reusable cannula assembly 120, as described below.

The reusable cannula assembly 120 includes a distal end 122 and a proximal end 124. The distal end 122 is connected to the proximal end 124 via a shaft portion 126. The distal end 122 includes a plurality of articulation linkages 128. The articulation linkages 128 may be equally spaced apart from each other. The articulation linkages 128 may be flexible segments, which are of equal length relative to each other or which are of different length relative to each other. The plurality of articulation linkages 128, distally disposed, facilitate the bending of a portion of the surgical instrument 130 via the controller 112, described below. Additionally, the reusable cannula assembly 120 may include linkages 129 that are not controlled by the controller 112. The linkages 129 may define a pre-set bend actuated by operating switch 115.

The surgical instrument 130 includes an end effector assembly 132 at its distal end and an actuation mechanism 138 at its proximal end 134. The end effector assembly 132 is connected to the actuation mechanism 138 via a flexible shaft portion 136.

The end effector assembly 132 of the surgical instrument 130 may include a pair of opposed jaw members such that at least one of the jaw members is induced to move relative to the other jaw member between open and close positions in response to manipulation of the reusable handle assembly 110.

It is noted that the entire surgical instrument 130 may be slidable inserted through and locked into the reusable handle assembly 110 or that a portion of the surgical instrument 130 may be slidable inserted through and locked within the reusable handle assembly 110. FIG. 4C, described below, illustrates a portion of the surgical instrument 130 protruding from the reusable handle assembly 110.

In operation, the reusable cannula assembly 120 is configured to be operatively connected to and steerable by the reusable handle assembly 110. The proximal end 124 of the reusable cannula assembly 120 is connected to the mating mechanism 116 of the reusable handle assembly 110. After the connection of the reusable cannula assembly 120 and the reusable handle assembly 110 takes place, the surgical instrument 130 is configured to be inserted through the reusable handle assembly 110 and configured to advance a length of the reusable cannula assembly 120. The surgical instrument 130 is configured to engage with the trigger mechanism 118 of the reusable handle assembly 110.

It is noted that the handle assembly 110, the cannula assembly 120, and the surgical instrument 130 are modular components configured to be releasably coupled/connected/attached to each other. The mating mechanism 116 enables snapping or interconnecting with the cannula portion 125. The mating mechanism 116 may include a plurality of spaced protrusions and a plurality of spaced recesses for enabling snapping or interconnecting with the reusable handle assembly 110. The cannula portion 125 may also include a plurality of protrusions and/or recesses for enabling its connection with the mating mechanism 116. It is noted that the connection is a releasable or removable or detachable connection, in order to allow the components to be modular components. Thus, releasable securement is caused by the mechanical mating mechanism 116, which may be incorporated on proximal and/or distal ends of the reusable handle assembly 110, the reusable cannula assembly 130, and/or the surgical instrument 130.

Referring to FIG. 2A, a cut-away view 200A of the reusable handle assembly is presented, whereas referring to FIG. 2B, a side view 200B of the reusable handle assembly is presented, in accordance with the present disclosure.

FIG. 2A depicts the batteries 210 and the electronic circuitry 220 positioned within the handle portion 119 of the reusable handle assembly 110. The reusable handle assembly 110 is configured to include the battery pack 210 and the motor 114 incorporated therewith for powering the surgical system 100 (see FIG. 1). Additionally, FIG. 2A depicts the controller 112, which is in electrical communication with the batteries 210 and the trigger mechanism 118, which is in mechanical cooperation with the motor/cannula assembly interface 230. The electronic circuitry 220 is configured to electrically communicate with at least one processor for enabling flow of electrosurgical energy between the battery pack 210 and the motor 114.

FIG. 2B depicts the relative positions of the motor 114, the trigger mechanism 118, the controller 112, and the switch 115 with respect to the handle portion 119. Once again, the controller 112 may be a joystick mechanism that steers the articulation linkages 128 of the reusable cannula assembly 120 (see FIG. 1), which are distally disposed on the reusable cannula assembly 120.

It is also envisioned that battery pack 210 includes at least one disposable battery. The disposable battery may be between about 9 volts and about 30 volts and may be useful in a disposable surgical system configuration. Other power-supplying means are also contemplated including electric power. In alternative embodiments a cord is provided to connect the surgical system 100 to a generator. Additionally, the surgical system 100 may be wirelessly connected to a power source.

Referring to FIG. 3A, a perspective view of the reusable cannula assembly, in accordance with the present disclosure is presented. Referring to FIG. 3B, a magnified interior view of a proximal end of the reusable cannula assembly of FIG. 3A, in accordance with the present disclosure is presented.

FIGS. 3A and 3B pertain to the interior view 300 of the reusable cannula assembly 120. The proximal end 124 of the reusable cannula assembly 120 may be referred to as the articulation assembly 124. The articulation assembly 124 includes racks 320 that attach to cables 310 to steer the articulation linkages 128, distally disposed. The articulation assembly 124 also includes a motor interface 330 and lead screws 340 driven by the motor 114 (see FIG. 2B). Additionally, the shaft portion 126 may be a flexible portion which houses the cables 310. Therefore, the reusable cannula assembly 120 includes an articulation assembly 124 at a proximal end thereof for interfacing with at least one cable 310 for steering the plurality of articulation linkages 128, which are distally disposed on the reusable cannula assembly 120.

Referring to FIGS. 4A-4C, perspective views of the surgical instrument system of FIG. 1, illustrating how the handle assembly, cannula assembly, and surgical instrument are releasably coupled/connected/attached to each other, in accordance with the present disclosure is presented.

FIGS. 4A-4C illustrate the connection mechanism 400 of the modular components. In a first step 410, shown in FIG. 4A, the modular cannula assembly 120 snaps into or releasably interconnects with the modular handle assembly 110. In a second step 420, shown in FIG. 4B, the surgical instrument 130 snaps into or releasably interconnects within the modular handle assembly 110. In the third step 430, shown in FIG. 4C, the surgical instrument 130 is slidably inserted through the modular cannula assembly 120. In the fourth step 440, shown in FIG. 4C, the surgical instrument 130 releasably or removably engages with the trigger mechanism 118 of the modular handle assembly 110.

Therefore, one method of the exemplary embodiments includes releasably securing the modular handle assembly 110 to the modular cannula assembly 120, the modular handle assembly 110 including a joystick controller 112, a self-contained battery pack 210, electronic circuitry 220, and the motor 114, inserting at least one surgical instrument 130 through the modular handle assembly 110, advancing the at least one surgical instrument 130 a length of the modular cannula assembly 120, releasably securing the at least one surgical instrument 130 to the modular handle assembly 110 and steering the modular cannula assembly 120 via the joystick controller 112 of the modular handle assembly 110 so as to actuate the at least one surgical instrument 130.

In an alternative embodiment, the reusable handle assembly 110 may include at least one sensor positioned thereon or therewith. For example, electrical contacts, proximity sensors, optical sensors, photo diodes, and/or mechanical or metallic sensors may be used to control and/or record information concerning the end effector assembly 132 or the articulation linkages 128 distally disposed or the coupling relationships established between the components of the surgical system 100.

In yet another alternative embodiment, the reusable handle assembly 110 may include at least one indicator configured to indicate at least one parameter related to the reusable cannula assembly 120 and the surgical instrument 130.

The at least one indicator may be either a numerical indicator or a color indicator or a combination thereof.

The at least one parameter may relate to positional orientations of a plurality of articulation linkages 128 distally disposed on the reusable cannula assembly 130, may relate to battery pack life, may relate to end-of-life of the reusable handle assembly 110 after a predetermined number of replacements exceed a predetermined limit, may relate to actuations of the surgical instrument 130, and may also relate to coupling relationships established between the reusable handle assembly 110, the reusable cannula assembly 120, and the surgical instrument 130.

Additionally, the load or loads on battery pack 210 and motor 114 of powered surgical system 100 are determined to control a motor speed if the load or loads indicate a damaging limitation is reached or approached. For example, the energy remaining in battery pack 210, the number of firings remaining, whether battery pack 210 must be replaced or charged, and/or approaching the potential loading limits of powered surgical system 100 may be determined.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical system comprising:
   a reusable handle assembly having a controller and an electrical switch;
   a reusable cannula assembly steerable by the reusable handle assembly, the reusable cannula assembly being a tubular member defining a lumen therethrough, the reusable cannula assembly having first linkages and second linkages formed on sections of the tubular member; and
   a plurality of surgical instruments configured to be inserted through the reusable handle assembly and configured to advance through the reusable cannula assembly from a proximal end to a distal end thereof such that the plurality of surgical instruments are engaged with at least one trigger mechanism of the reusable handle assembly;

wherein the reusable handle assembly, the reusable cannula assembly, and the plurality of surgical instruments are modular components configured to be releasably coupled to each other; and wherein the first linkages have a first linear configuration and a second pre-set bent configuration, the first linkages configured to transition from the linear configuration to the pre-set bent configuration in response to activation of the electrical switch of the reusable handle, the second linkages articulating in response to the controller.

2. The surgical system according to claim 1, wherein the reusable handle assembly is configured to include a self-contained battery pack and a motor incorporated therewith for powering the surgical system.

3. The surgical system according to claim 2, wherein the reusable handle assembly is configured to include electronic circuitry electrically communicating with at least one processor for enabling flow of electrosurgical energy between the self-contained battery pack and the motor.

4. The surgical system according to claim 1, wherein the controller of the reusable handle assembly is a joystick mechanism configured to steer the second linkages.

5. The surgical system according to claim 1, wherein the proximal end of the reusable cannula assembly is slidably inserted into a mating mechanism of the reusable handle assembly.

6. The surgical system according to claim 1, wherein the second linkages include first and second segments, the first segment having a length equal to a length of the second segment.

7. The surgical system according to claim 1, wherein the second linkages are flexible segments.

8. The surgical system according to claim 1, wherein the proximal end of the reusable cannula assembly includes an articulation assembly for interfacing with at least one cable for steering the second linkages.

9. The surgical system according to claim 1, wherein at least one surgical instrument of the plurality of surgical instruments includes a proximal end, a flexible shaft connected to the proximal end, and an end effector assembly connected at a distal end of the flexible shaft.

10. The surgical system according to claim 9, wherein the at least one surgical instrument of the plurality of surgical instruments is configured to include at least one mechanical mating mechanism for mating with the reusable handle assembly.

11. The surgical system according to claim 10, wherein the at least one mechanical mating mechanism of the at least one surgical instrument of the plurality of surgical instruments includes a plurality of spaced protrusions and a plurality of spaced recesses for enabling snapping or coupling with the reusable handle assembly.

12. The surgical system according to claim 9, wherein the end effector assembly includes a pair of opposed jaw members such that at least one of the jaw members is induced to move relative to the other jaw member between open and closed positions in response to manipulation of the reusable handle assembly.

13. The surgical system according to claim 1, wherein the reusable handle assembly includes at least sensor positioned thereabout.

14. The surgical system according to claim 1, wherein the reusable handle assembly includes at least one indicator configured to indicate at least one parameter related to the reusable cannula assembly and the plurality of surgical instruments.

15. The surgical system according to claim 14, wherein the at least one indicator is selected from a group consisting of a numerical indicator and a color indicator or a combination thereof.

16. The surgical system according to claim 14, wherein the at least one parameter relates to positional orientations of the second linkages.

17. The surgical system according to claim 14, wherein the at least one parameter relates to battery pack life.

18. The surgical system according to claim 14, wherein the at least one parameter relates to end-of-life of the reusable handle assembly after a predetermined number of replacements exceed a predetermined limit.

19. The surgical system according to claim 14, wherein the at least one parameter relates to actuations of the plurality of surgical instruments.

20. The surgical system according to claim 14, wherein the at least one parameter relates to coupling relationships between the reusable handle assembly, reusable cannula assembly, and the plurality of surgical instruments.

21. A surgical system comprising:
a reusable handle assembly having a controller, an electrical switch, and a mating mechanism;
a reusable cannula assembly steerable by the reusable handle assembly, the reusable cannula assembly having first linkages and second linkages formed on an outer surface of the reusable cannula assembly, the reusable cannula assembly having a proximal end slidably insertable into the mating mechanism to interconnect the reusable cannula assembly and the reusable handle assembly; and
a plurality of surgical instruments configured to be inserted through the reusable handle assembly and configured to advance through the reusable cannula assembly from a proximal end to a distal end thereof such that the plurality of surgical instruments are engaged with at least one trigger mechanism of the reusable handle assembly,
wherein the first linkages are configured to transition from a first linear configuration to a second pre-sent bent configuration in response to activation of the electrical switch, and wherein the second linkages are configured to articulate independent of the first linkages.

* * * * *